United States Patent
Lim et al.

(10) Patent No.: US 7,555,930 B2
(45) Date of Patent: Jul. 7, 2009

(54) TEST ASSEMBLY AND METHOD

(75) Inventors: Jui Jing Lim, Singapore (SG); Kok Tong Soh, Singapore (SG); Hee Ching Ho, Singapore (SG); Ying Su, Singapore (SG)

(73) Assignee: Seagate Technology LLC, Scotts Valley, CA (US)

( * ) Notice: Subject to any disclaimer, the term of this patent is extended or adjusted under 35 U.S.C. 154(b) by 0 days.

(21) Appl. No.: 11/779,521

(22) Filed: Jul. 18, 2007

(65) Prior Publication Data

US 2009/0019917 A1 Jan. 22, 2009

(51) Int. Cl.
*G01N 3/30* (2006.01)
(52) U.S. Cl. ...................................... 73/12.06
(58) Field of Classification Search ..... 73/12.01–12.14, 73/865.3
See application file for complete search history.

(56) References Cited

U.S. PATENT DOCUMENTS

| | | | | |
|---|---|---|---|---|
| 3,805,900 A | * | 4/1974 | Sainsbury | 175/20 |
| 4,640,120 A | * | 2/1987 | Garritano et al. | 73/12.13 |
| 4,696,182 A | * | 9/1987 | Meir | 73/12.07 |
| 5,635,624 A | * | 6/1997 | Cerny | 73/12.01 |
| 6,522,998 B1 | * | 2/2003 | Mazur et al. | 703/8 |
| 6,983,638 B2 | * | 1/2006 | Yetukuri et al. | 73/12.04 |
| 7,219,531 B2 | * | 5/2007 | Hammons et al. | 73/12.13 |
| 7,320,242 B2 | * | 1/2008 | Hoo Fatt et al. | 73/12.14 |
| 7,373,801 B2 | * | 5/2008 | Friedman et al. | 73/12.06 |
| 2004/0040369 A1 | * | 3/2004 | Hoo Fatt et al. | 73/12.01 |
| 2004/0200264 A1 | | 10/2004 | Chen et al. | 73/12.06 |
| 2004/0203446 A1 | | 10/2004 | Seung | 455/67.11 |
| 2005/0081656 A1 | * | 4/2005 | Saari et al. | 73/865.3 |
| 2006/0207311 A1 | * | 9/2006 | Hammons et al. | 73/12.13 |

FOREIGN PATENT DOCUMENTS

CN 2003-166922 6/2003

* cited by examiner

*Primary Examiner*—Max Noori
(74) *Attorney, Agent, or Firm*—Westman, Champlin & Kelly, P.A.

(57) ABSTRACT

A test apparatus and method are disclosed. The test apparatus disclosed includes an accelerator assembly and holder assembly that releasably holds a test specimen for acceleration along an acceleration path. Following acceleration along the acceleration path, the test specimen is released from the holder assembly and drops to a landing. The landing can be formed of different materials and at different orientations depending upon the test specifications. Following impact with the landing, the shock robustness of the test specimen is determined to generate shock robustness data. In embodiments disclosed, shock data is used to design shock absorber components for the test specimen or product.

20 Claims, 13 Drawing Sheets

TEST ASSEMBLY AND METHOD

BACKGROUND

Electronic products and in particular, portable electronic products, are susceptible to being dropped, for example, from a table or other surface. Dropped products can land on a hard floor or other hard landing surface. To limit or reduce damage due to impact, shock absorber components or devices are used to protect electronic components from damage. The design of the shock absorber components effects shock robustness of the electronic products on different landing surfaces. Mathematical modeling techniques can be used to design shock absorber components to enhance shock robustness. Such modeling techniques however are cumbersome and often times do not predict actual shock robustness of the product. Embodiments of the present invention provide solutions to these and other problems, and offer other advantages over the prior art.

SUMMARY

A test apparatus is used to enhance shock robustness and shock performance for electronic products. The test apparatus includes an accelerator assembly and a holder assembly that releasably holds a test specimen for acceleration along an acceleration path. Following acceleration along the acceleration path, the test specimen is released from the holder assembly and drops to a landing. The landing can be formed of different materials and at different orientations depending upon the test specifications. Following impact with the landing, the shock robustness of the test specimen is determined to generate shock data. In the illustrated embodiments, the shock data is used to design shock absorber components for the test specimen or product. Other features and benefits that characterize embodiments of the present invention will be apparent upon reading the following detailed description and review of the associated drawings.

DETAILED DESCRIPTION OF ILLUSTRATIVE EMBODIMENTS

Figure 1:
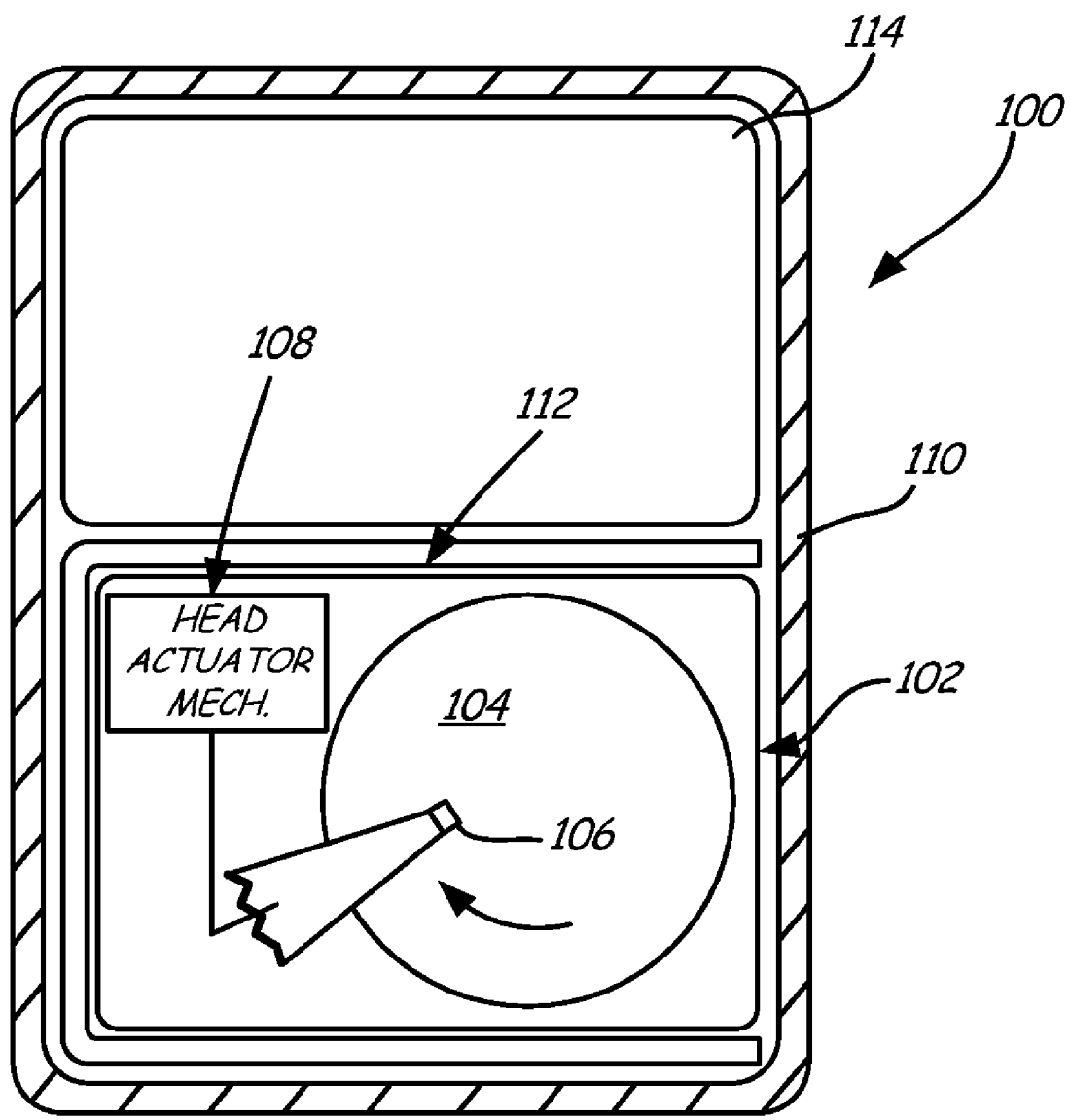
FIG. 1 is an embodiment of a portable electronic device having a shock absorber component.

FIG. 1 schematically illustrates an electronic device 100 that includes a shock absorber component to protect the electronic device from damage as a result of being dropped. In the illustrated embodiment the electronic device 100 includes a data storage device 102 which includes one or more rotatable discs 104 to store digitally encoded data. The illustrated data storage device includes a head 106 to read data from or write data to the one or more rotating discs 104. The head 106 is positioned via a head actuator mechanism 108 based upon commands from a host system. In the illustrated embodiment, the data storage device 102 is contained in a product casing 110. Illustratively, the product casing 110 is formed of a plastic material, however application is not limited to a particular material nor a plastic material and is applicable to any material used to form a housing. An external shock absorber component 112 is fitted about the data storage device 102 between the data storage device 102 and product casing 110 to absorb shock impact to the data storage device 102. In the illustrated embodiment, the electronic device 100 includes a host component 114 enclosed in the product casing 110 which illustratively forms a portable play device such as an MP3 play device or other device with data storage.

Figure 2:
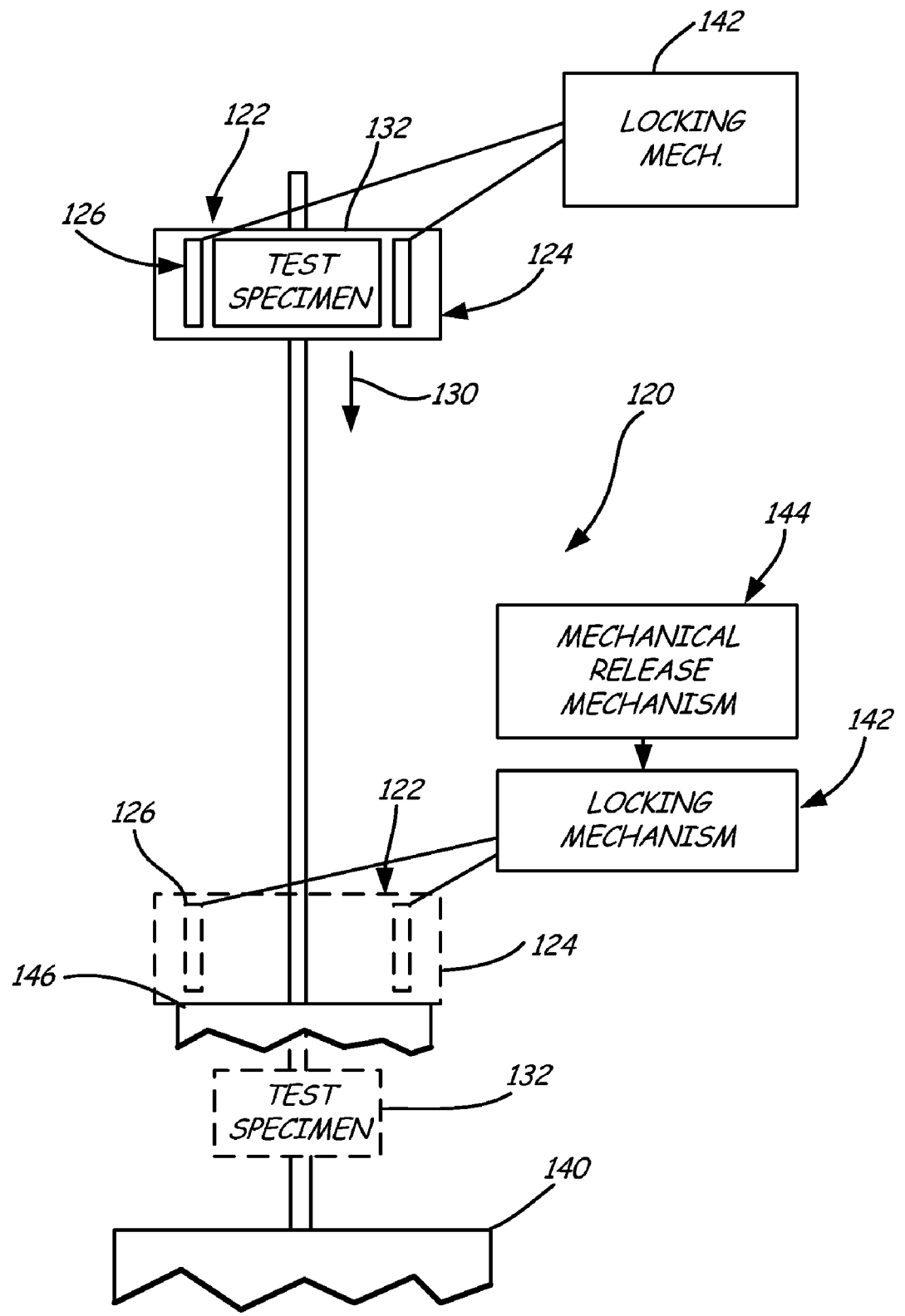
FIG. 2 is a schematic illustration of a test apparatus, which can be used to test effectiveness of the shock absorber component of the device of FIG. 1.

The shock absorber 112 of the device 100 illustrated in FIG. 1 can be designed using mathematical modeling techniques to predict performance. However, predicted performance of the mathematically modeled component may not match actual shock performance of the device. FIG. 2 schematically illustrates a test apparatus 120 to impart a drop force or shock to determine actual shock performance of a shock absorber component, such as that illustrated in FIG. 1, or other shock absorber component. As shown in FIG. 2, the apparatus includes an accelerator assembly 122 that includes an accelerator component 124 and a releasable holder assembly 126 coupled to the accelerator component 124. As shown, the accelerator component 124 is movable along an acceleration path as illustrated by arrow 130 to impart an acceleration force to a test specimen 132 (illustrated schematically) secured to the holder assembly 126.

As shown, following acceleration along the acceleration path, the test specimen 132 is released from the holder assembly 126 to drop to a landing 140 as illustrated in phantom in FIG. 2. Landing 140 can be formed of various materials to test shock performance for different surfaces and at different orientations. In the illustrated embodiment, the test specimen 132 is secured in the holder assembly 126 via a locking mechanisms 142 while the test specimen 132 is moved along the acceleration path. Following acceleration, the test specimen 132 is released from the holder assembly 126 via a mechanical release mechanism 144 that releases the locking mechanism 142 at elevation 146 so that the test specimen 132 drops to the landing 140.

Figure 3:
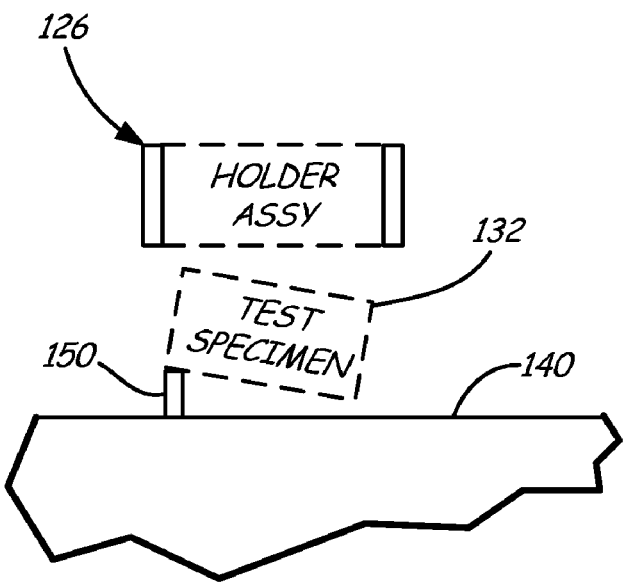
FIG. 3 schematically illustrates a landing for an embodiment of the apparatus illustrated in FIG. 2.

FIG. 3 is a detailed illustration showing the test specimen 132 after the test specimen 132 is released from the holder assembly 126 and prior to impact with the landing 140. In the embodiment shown, the landing 140 includes a roll bar 150 elevated from the landing surface to induce a rotational shock to the test specimen 132 released from the holder assembly 126, however, the application is not limited to the embodiment shown in FIG. 3. Other components may be added or removed as needed for any particular test and application.

Figure 4:
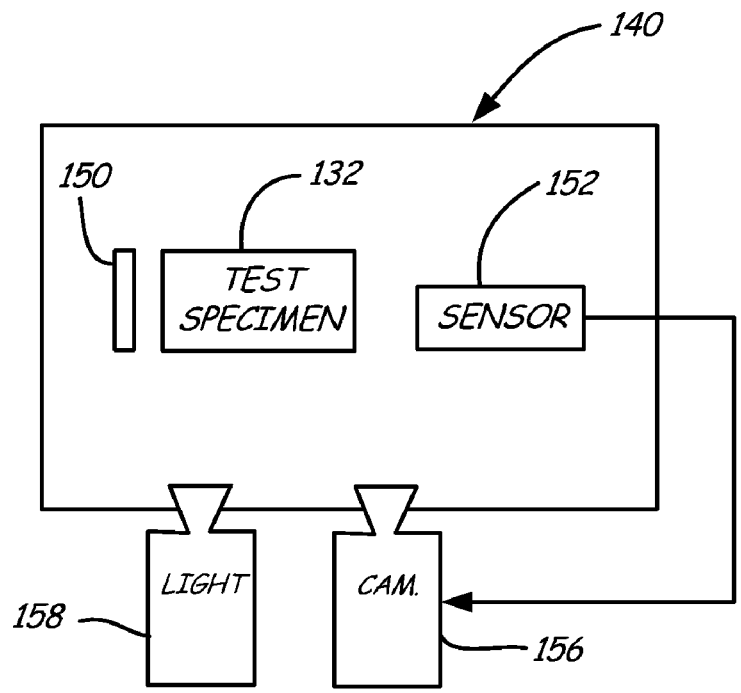
FIG. 4 schematically illustrates a camera assembly to capture shock impact between a test specimen and landing.

As shown in FIG. 4, a camera assembly is used to capture one or more images of the test specimen 132 as it impacts on the landing 140. The camera assembly includes a sensor 152 (illustrated schematically) which senses the presence of the test specimen 132 and activates a camera 156 to record one or more images of the test specimen as the test specimen 132 drops to the landing 140. Illustratively, the sensor 152 can be an accelerometer, although application is not limited to a particular sensor device. As shown, the camera assembly includes a light source 158 to illuminate the landing area. In one embodiment, the camera is a video camera that is programmed to take a series of digital images of the test specimen 132 as it drops and impacts the landing 140. In the illustrated embodiment, sensor 152 is supported on the landing surface, however, it should be understood that the sensor 152 can be supported on the roll bar 150 or other elevated surface of the apparatus.

Figure 5:
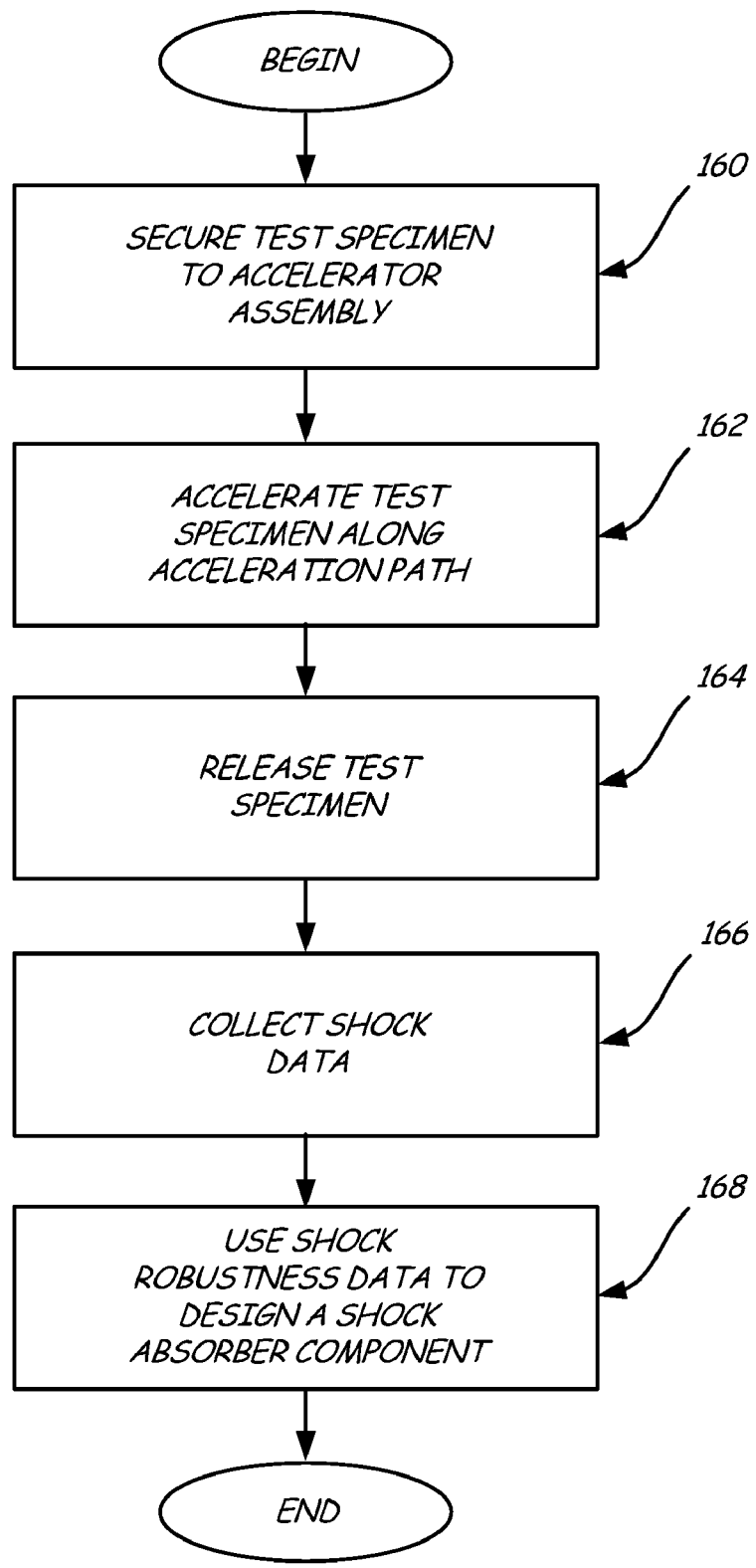
FIG. 5 is a flow chart illustrating steps for designing a shock absorber component.

As described, the test apparatus 120 is used to collect data relating to the shock effectiveness of a shock absorber component, such as component 112 of the electronic device illustrated in FIG. 1. The shock data is used to design shock absorber components having optimum shock absorbing performance. FIG. 5 illustrates steps for enhancing shock robustness and shock performance using the apparatus of the type illustrated in FIG. 2. As shown in step 160, a test specimen 132, such as a disc drive device (or other electronic device 100) is secured to the accelerator assembly 122 of the test apparatus 120. The test specimen 132 is secured to the accelerator assembly 122 via the holder assembly 126. In step 162, the test specimen 132 is accelerated along the acceleration path. In embodiments described, the test specimen 132 is secured to the holder assembly 126 via locking mechanism 142 while the test specimen 132 is moved along the acceleration path.

Following acceleration, the test specimen 132 is released from the holder assembly 126 as illustrated in step 164. The released test specimen 132 drops to the landing 140 to impart a shock force to the test specimen 132. Following the shock event, shock data is collected relating to the effectiveness or robustness of the shock absorber component as shown in step 166. In step 168, the collected data is used to design the shock absorber component 112. For the example of a disc drive or data storage device, the shock data includes whether the data storage device "bottoms-out" or hits the casing 110 during the shock event and/or whether latches of the head actuator mechanism 108 become unlatched. Based upon the shock data, the shock absorber component 112 is designed to limit contact or damage to the electronic components.

Figure 6:
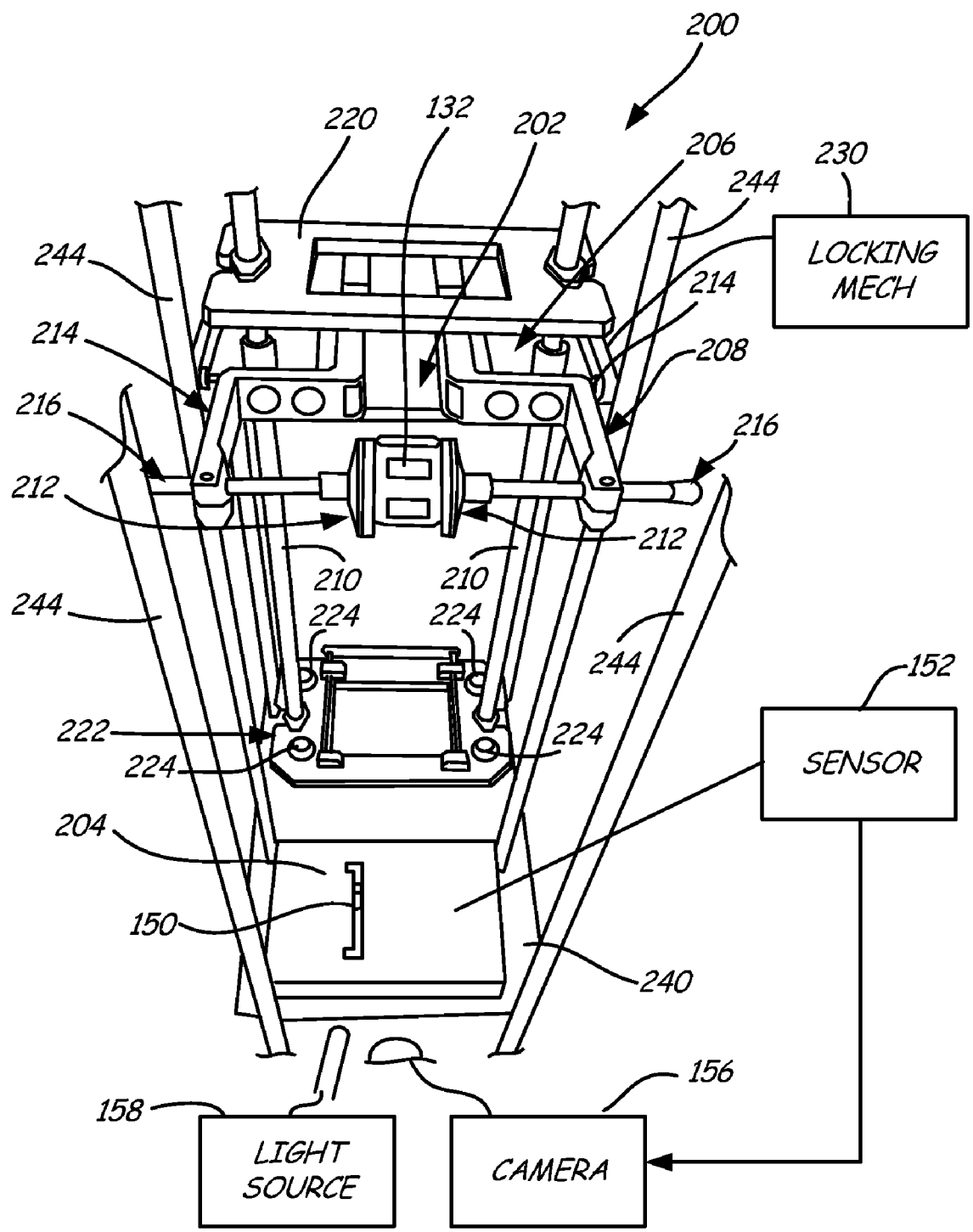
FIG. 6 is an illustration of another embodiment of a test apparatus to impart a shock force or input to a test specimen.

FIG. 6 illustrates an embodiment of a test apparatus 200 including an accelerator assembly 202 to accelerate test specimen 132 prior to dropping the test specimen 132 on a landing surface 204 as previous described with respect to FIG. 2. The accelerator assembly 202 includes an accelerator component 206 and holder assembly 208. The accelerator component 206 is movable along guide rails 210 to accelerate the test specimen along an acceleration path prior to dropping the test specimen 132 on the landing 204 of the apparatus. The test specimen 132 is secured to the accelerator component 206 through the holder assembly 208. In the illustrated embodiment the holder assembly 208 includes opposed clamps 212 coupled to clamp arms 214. Clamps 212 include a head portion designed to squeezably hold the test specimen 132. The spacing between the head portions of the clamps 212 is adjusted by slidably adjusting rods 216 slideable coupled to the clamp arms 214. Rods 216 are slid in an outward direction to expand the spacing between the opposed head portions to insert the test specimen 132. Rods 216 are slid inwardly to squeeze the test specimen 132 between the head portions of the clamps 212 to secure the test specimen 132 to the accelerator component 206 for testing.

In the illustrated embodiment, the acceleration path of the accelerator component 206 is defined between an upper platform 220 and lower platform 222. The lower platform 222 is spaced below the upper platform 220 and is elevated above landing 140 to form an end stop for the accelerator component 206. Thus, the accelerator component 206 moves from the upper platform 220 under the influence of gravity until the accelerator component 206 contacts the lower platform 222 at the end of the acceleration path. In the illustrated embodiment, the lower platform 222 includes bumpers 224 to absorb the impact force of the accelerator component 206 at the end of the acceleration path.

Following acceleration along the acceleration path, the test specimen 132 is released from the holder assembly 208. During acceleration along the acceleration path the test specimen 132 is retained in the holder assembly 208 via a locking mechanism 230 as previously described. Following release from the holder assembly 208, the test specimen 132 drops to landing 204. The landing 204 can be formed of various materials depending upon the test specifications. In the illustrated embodiment, the landing 204 includes elevated roll bar 150 (as previously described in FIG. 3) to induce a rotational shock to the released test specimen 132 for test operations. In the illustrated embodiment, the apparatus includes two guide rails 210, however application is not limited to the specific number of guide rails shown. The guide rails 210 and other components of the test apparatus 200 are supported relative to a support base 240 of the test apparatus. A frame is coupled to the support base 240 to form an enclosure for components of the test apparatus. As shown, the frame includes a plurality of posts 244 that extend from the support base 240. Clear or transparent walls can be coupled to the posts 244 to form a see-through enclosure for observing and/or recording the test sequence for design applications.

Figure 7:
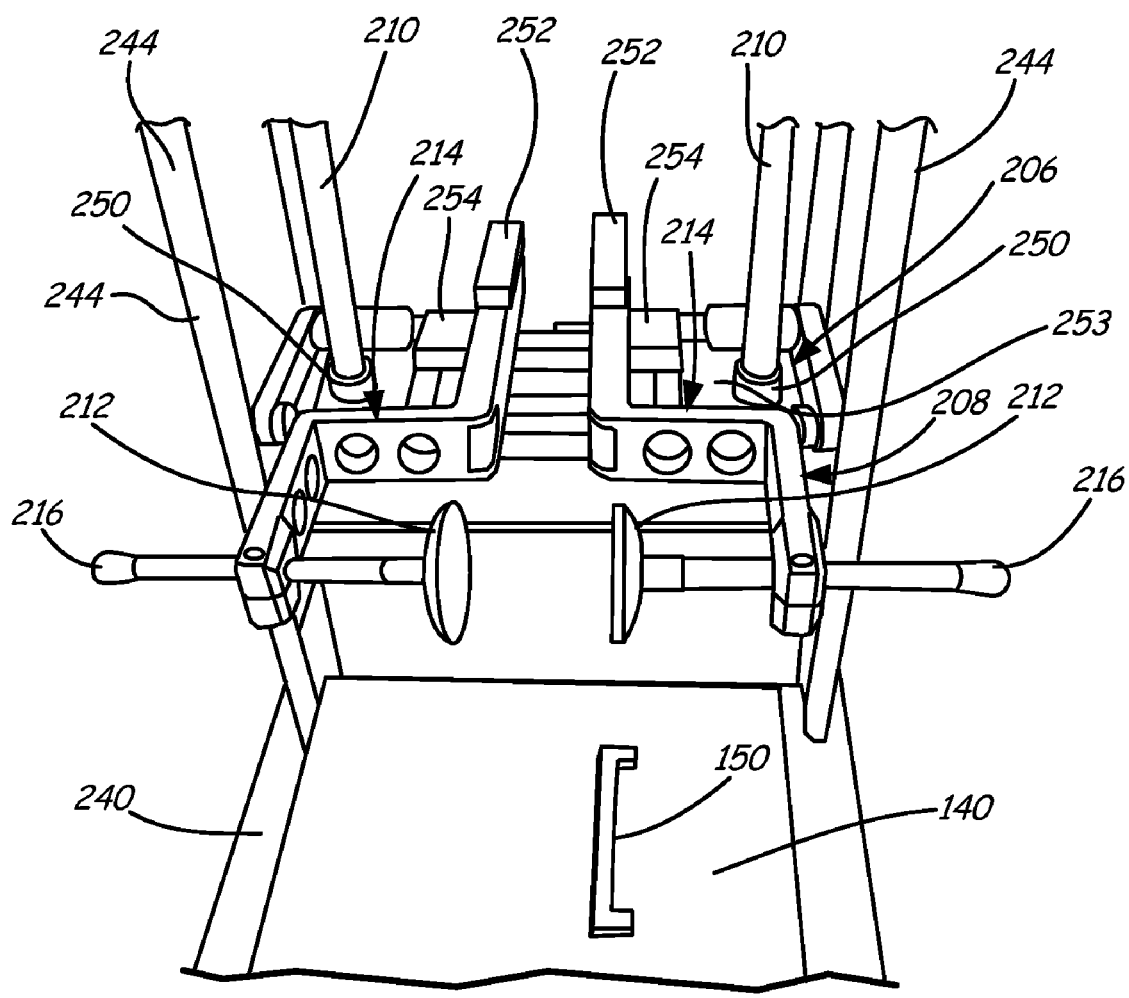
FIG. 7 is a detailed illustration of the accelerator component and holder assembly of the test apparatus of FIG. 6.

FIG. 7 is a detail illustration of an embodiment of the accelerator component 206 and the holder assembly 208. As shown, the accelerator component 206 includes linear bearings 250 that slide along rails 210 of the test assembly to move the accelerator component 206 along the acceleration path. One or more weights 252 are coupled to the accelerator component 206 to balance the accelerator component 206 and impart an acceleration force to the test specimen 132. The clamp arms 214 of the holder assembly 208 are coupled to a base plate 253 of the accelerator component 206 through a base portion 254 connected to the base plate 253 as shown more clearly in FIG. 8.

Figure 8:
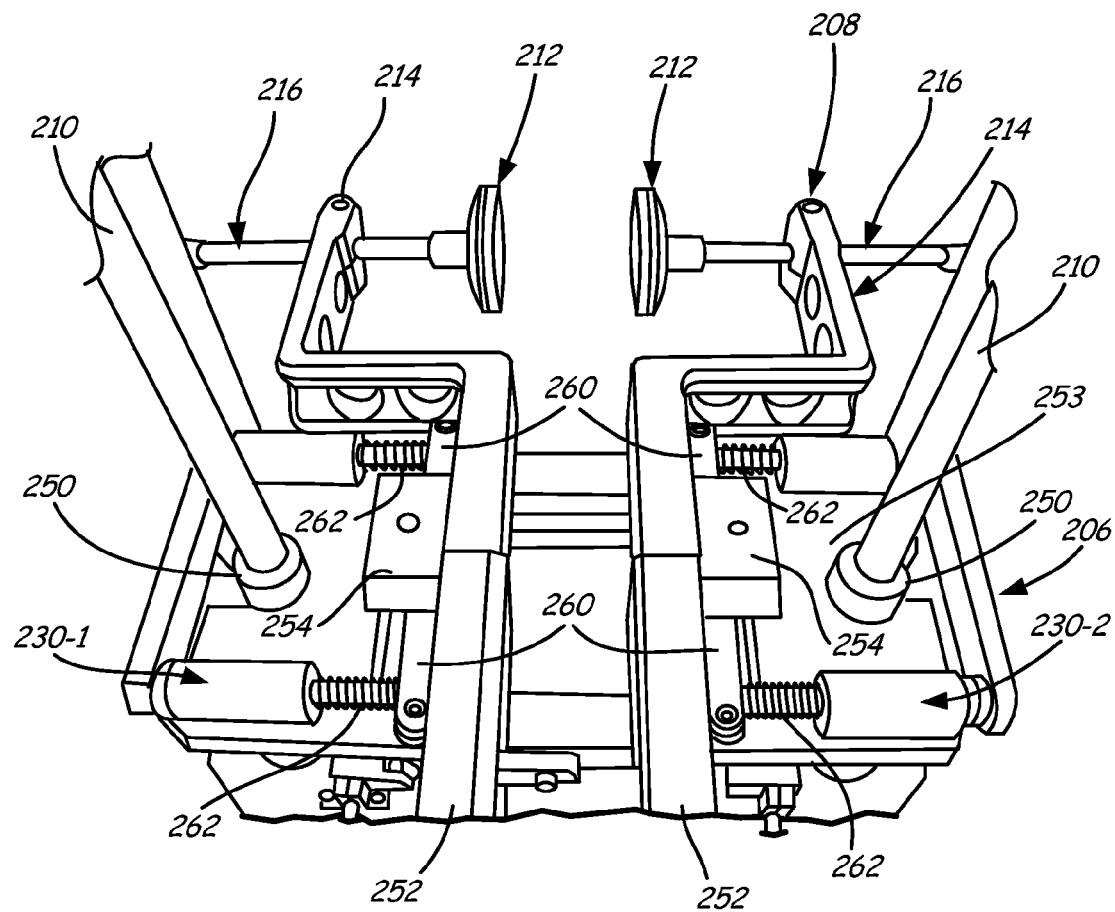
FIG. 8 is another illustration of the accelerator component and holder assembly of the test apparatus of FIG. 6.

In the illustrated embodiment shown in FIG. 8, clamp arms 214 are biased in the clamped position via the locking mechanism 230 (illustrated schematically in FIG. 6). In the embodiment shown, the locking mechanism includes locking mechanism assemblies 230-1, 230-2 coupled to each clamp arm 214 to maintain the clamp arms 214 in the clamped position while the test specimen 132 is accelerated along the acceleration path. As shown more clearly in FIG. 9, the locking mechanism assemblies 230-1, 230-2 bias the clamp arms 214 in the clamped position through flexible arms 260, which abut the clamp arms 214 of the holder assembly 208. In the illustrated embodiment, multiple flexible arms 260 abut each clamp arm 214. The position of the flexible arms 260 is adjusted via rods 262 coupled to the flexible arms 260.

Rods 262 are movable within supports 264 (shown in FIG. 9) between an inward clamping position and an outward position to selectively clamp and release the clamp arms 214. The rods 262 are biased in the clamping position by springs 266. Springs 266 are disposed about rods 262 and extend between supports 264 and the flexible arms 260. Rods 262 are moved against the spring bias to release the locking mechanism assemblies 230-1, 230-2 maintaining the clamp arms 214 in the clamped position. As shown in FIG. 10, flexible arms 260 are coupled to and extend from base portion 254 connected to the base plate 253. Clamp arms 214 are coupled to the base portion 254 and extend generally parallel to the flexible arms 260. Thus, inward movement of the rods 262 bias the flexible arms 260 and clamp arms 214 inwardly in the clamped position and outward movement of the rods 262 releases the clamp arms 214 from the clamped position. Although a particular locking mechanism is shown, application is not limited to multiple locking mechanism assemblies or the particular embodiment disclosed.

Figure 9:
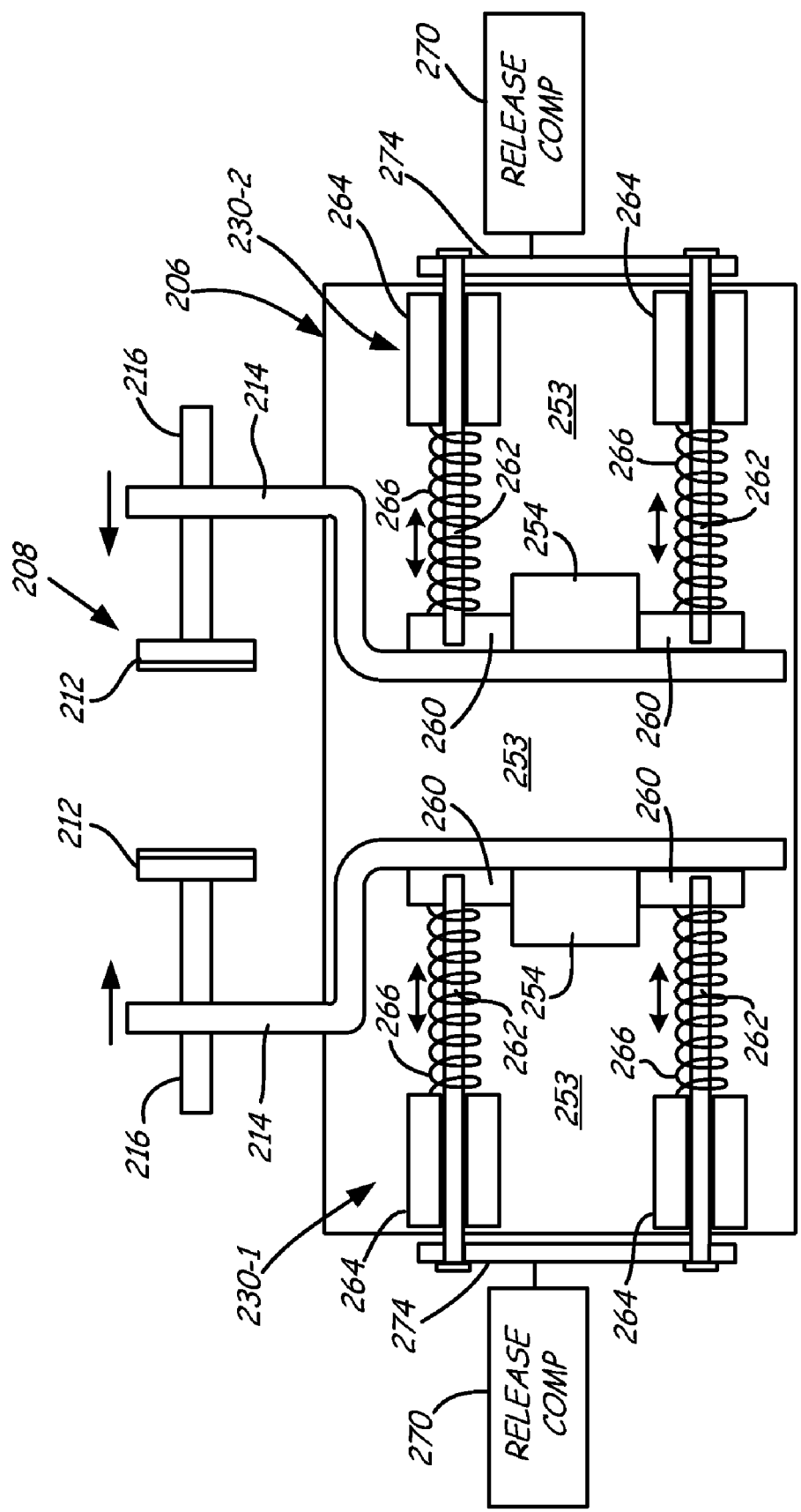
FIG. 9 is a schematic illustration of an embodiment of a locking mechanism and holder assembly for the test apparatus of FIG. 6.
Figure 10:
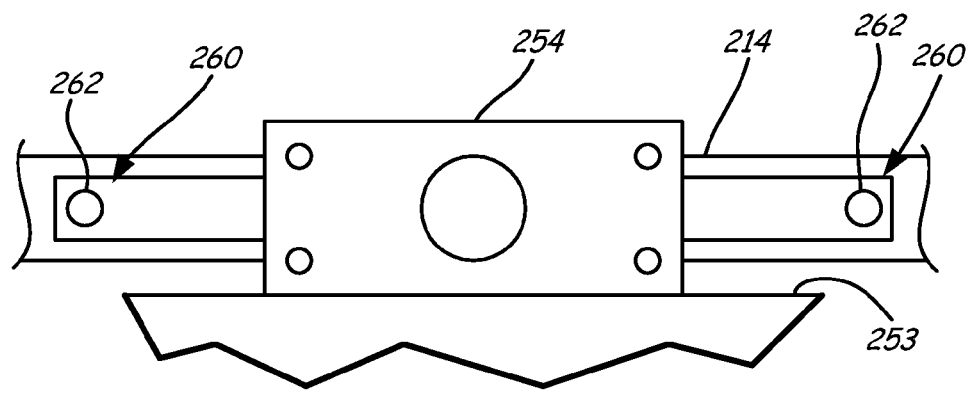
FIG. 10 illustrates an embodiment of a connection of the flexible arms and clamp arms to the base plate of the accelerator assembly.
Figure 11:
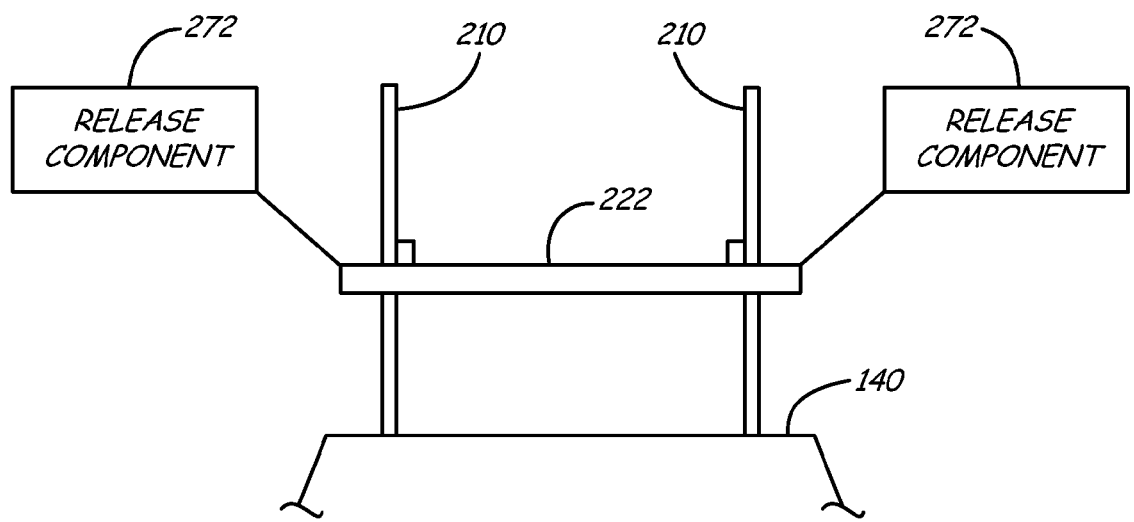
FIG. 11 is a schematic illustration of a release component off-board from the accelerator assembly.

The locking mechanism assemblies 230-1, 230-2 disclosed are released via a mechanical release mechanism which, in the illustrated embodiment, includes release components 270 on the accelerator component 206 as shown in FIG. 9 and release components 272 coupled to platform 222, off-board from the accelerator assembly as shown in FIG. 11. In the embodiment shown, the release components 270 on the accelerator component 206 are coupled to rods 262 through levers 274 (illustrated in FIG. 9) to move the rods 262 against the spring bias. Following acceleration, the release components 270 on the accelerator component 206 engage the release components 272 on the platform 222 to actuate levers 274 to move rods and arms 260, 262 outwardly against the spring bias to release the test specimen 132 so that the test specimen 132 drops to landing 140.

Figure 12:
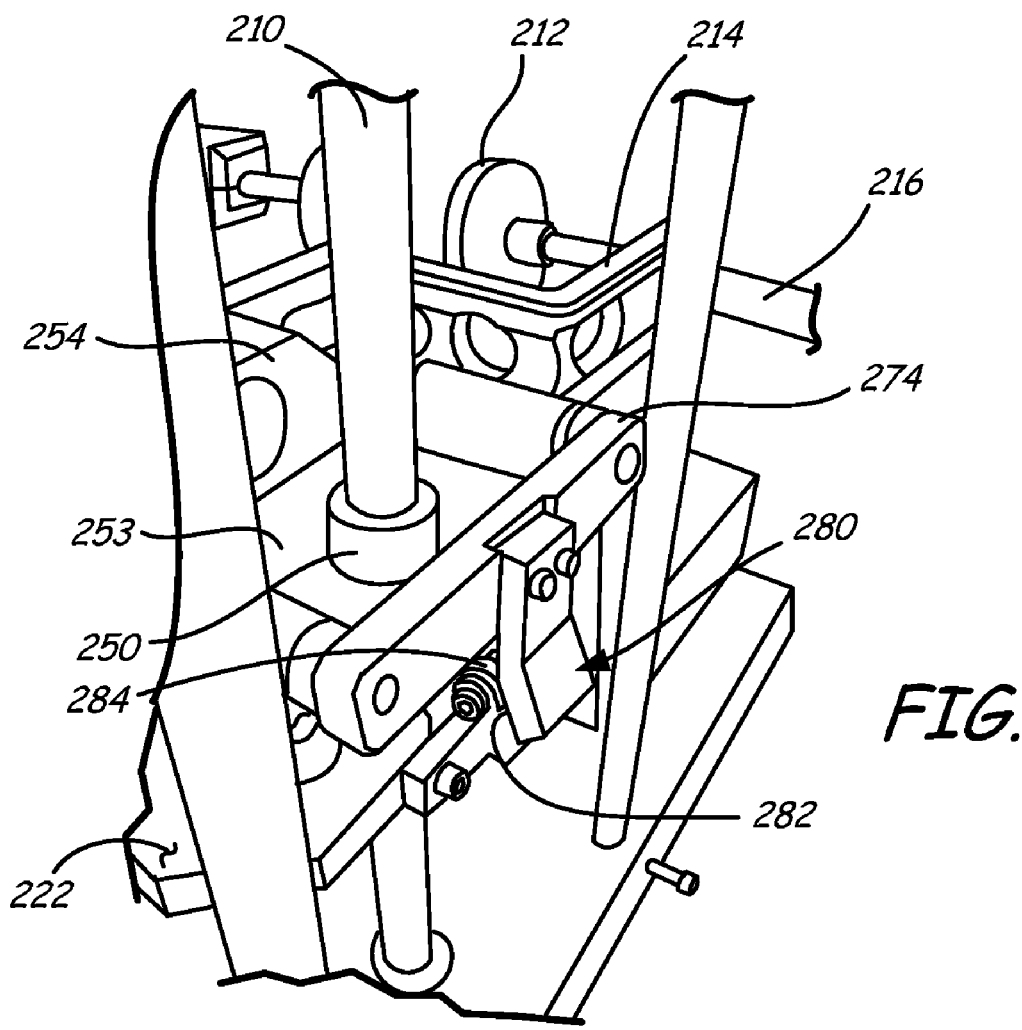
FIG. 12 illustrates an embodiment of camming assembly forming a mechanical release mechanism of an embodiment of the test apparatus.

In the embodiment illustrated in FIGS. 12-13A and 13B, the release mechanism includes a camming assembly 280 as shown in FIG. 12. In the illustrated embodiment, the camming assembly 280 includes inclined camming surfaces 282 formed on flanges extending from the levers 274 as shown in FIG. 12 (only one camming surface 282 is shown in FIG. 12) and a roller 284 formed on platform 222 elevated from the landing 204. The camming surfaces 282 contact rollers 284 on the platform 222 as shown in FIG. 12 to release the bias force on the clamp arms 214 imparted through the locking mechanism assemblies 230-1, 230-2. Although a particular release mechanism is shown, application is not limited to a camming assembly or the particular camming assembly shown.

Figure 13A:
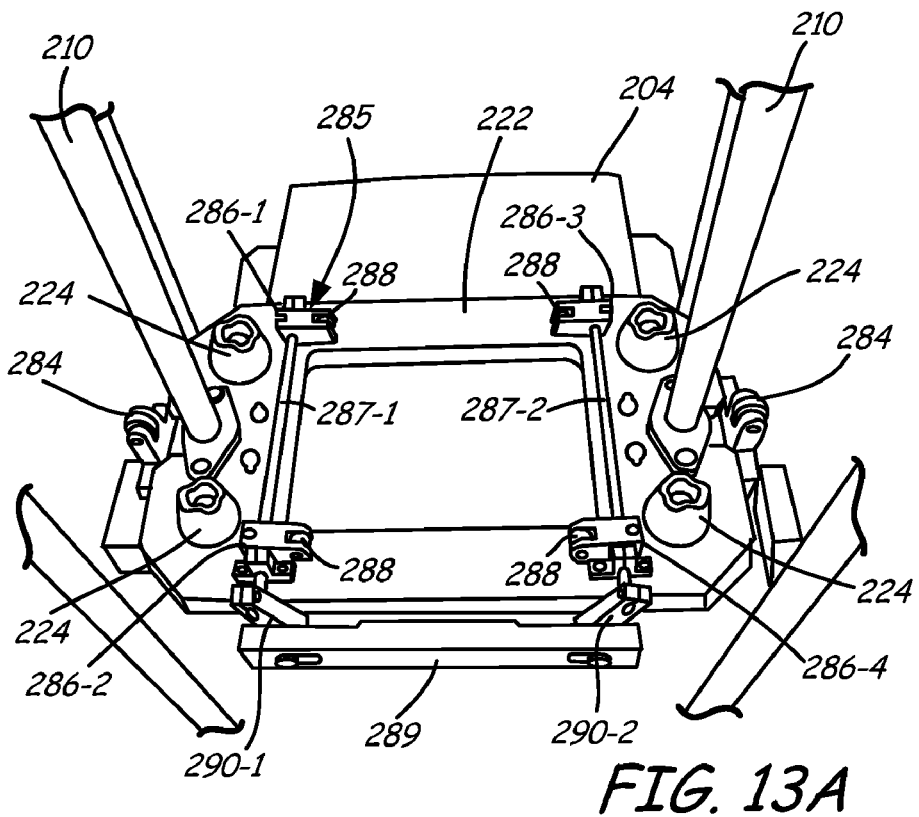
FIG. 13A illustrates a platform including rollers of the camming assembly of FIG. 12 and a lift assembly configured to raise the accelerator assembly or component above the platform.
Figure 13B:
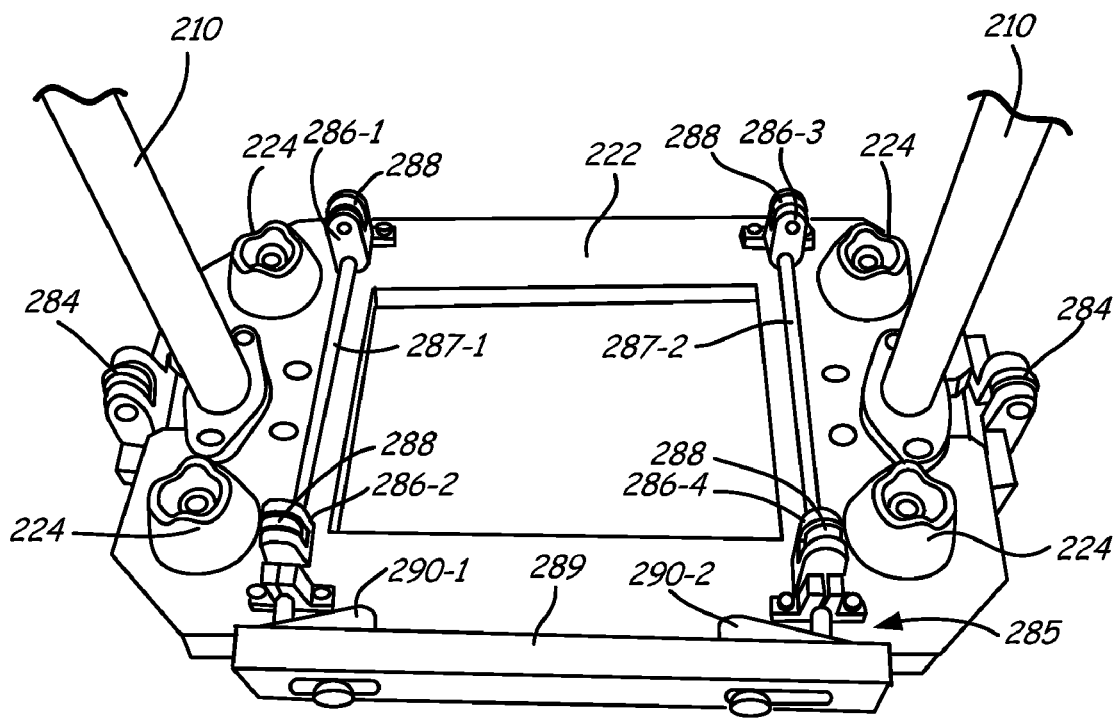
FIG. 13B illustrates the platform and lift assembly in a raised position.

As previously described, the accelerator component 206 moves along an accelerator path between platform 200 and platform 222. In the embodiment shown in FIGS. 13A and 13B, platform 222 includes a lift assembly 285 to lift the acceleration component 206 and holder assembly 208 above platform 222 to raise the accelerator component 206 to an elevated height for testing. As shown in FIGS. 13A and 13B, the lift assembly 285 includes blocks 286-1, 286-2, 286-3, 286-4 coupled to rods 287-1, 287-2 and rotatable therewith between a rest position shown in FIG. 13A and a lift position shown in FIG. 13B. In the rest position, the blocks 286-1, 286-2, 286-3, and 286-4 are recessed below bumpers 224 so that the accelerator component 206 rests on bumpers 224. In the lift position, the blocks 286-1, 286-2, 286-3, 286-4 are elevated above bumpers 224 to lift the accelerator component 206 from bumpers 224.

In the illustrated embodiment, the lift assembly 285 includes four blocks each having a roller 288 (shown in FIG. 13B) which abuts the accelerator component 206. Rods 287-1, 287-2 are rotated via bar 289 through linkages 290-1, 290-2, respectively. Bar 289 is moved from a first position shown in FIG. 13A to a second position shown in FIG. 13B. Movement of the bar 289 between the first position and the second position rotates rods 287-1, 287-2 through linkages 290-1, 290-2 to move the blocks 286-1, 286-2, 286-3, and 286-4 from the rest position, shown in FIG. 13A, to the lift position, shown in FIG. 13B as described.

Figure 14:
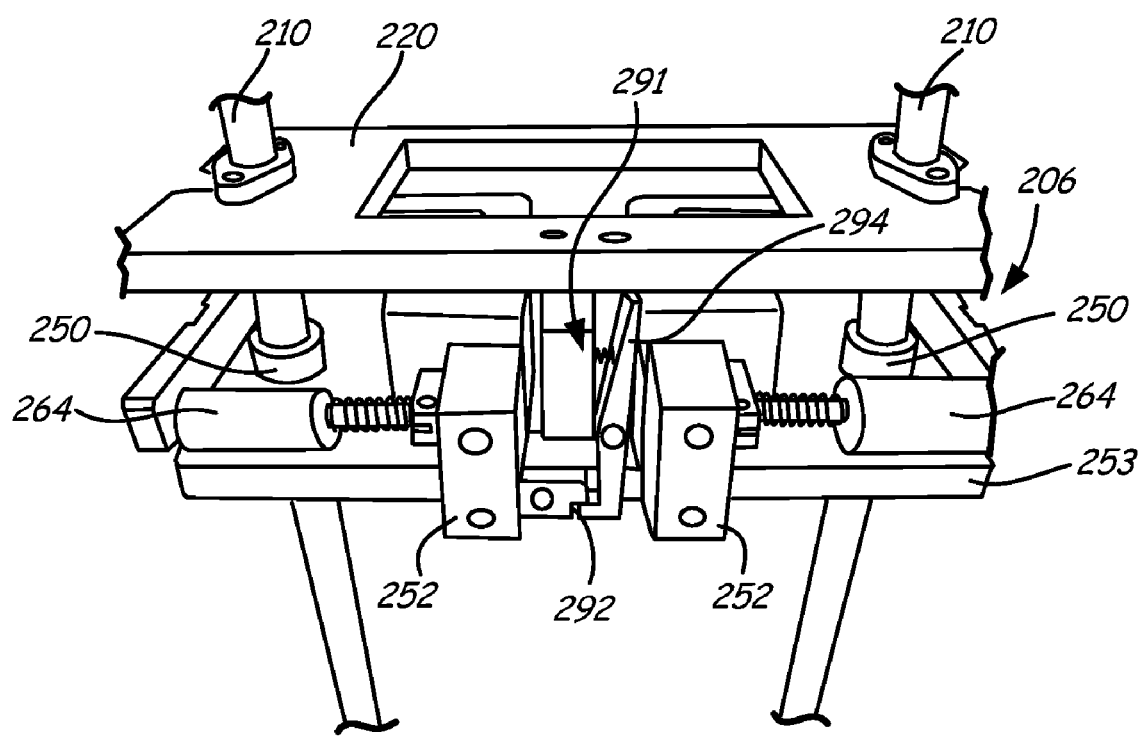
FIG. 14 illustrates an elevated platform and latching mechanism for latching the accelerator assembly to the elevated platform.

In the illustrated embodiment, the accelerator component 206 is latched to the platform 220 via a latch assembly 291 shown in FIG. 14. In the illustrated embodiment, the latch assembly 291 includes a notched latch surface 292 on the accelerator component 206 and a pivoting latch arm 294 coupled to platform 220. As shown, the pivoting latch arm 294 includes a latch surface which mates with the notched latch surface 292 on the accelerator component 206 in a latched position. The latch arm 294 is pivoted to separate the latch surface on the arm 294 from the notched latch surface 292 on the accelerator component 206 to release the test specimen for testing.

Figure 15:
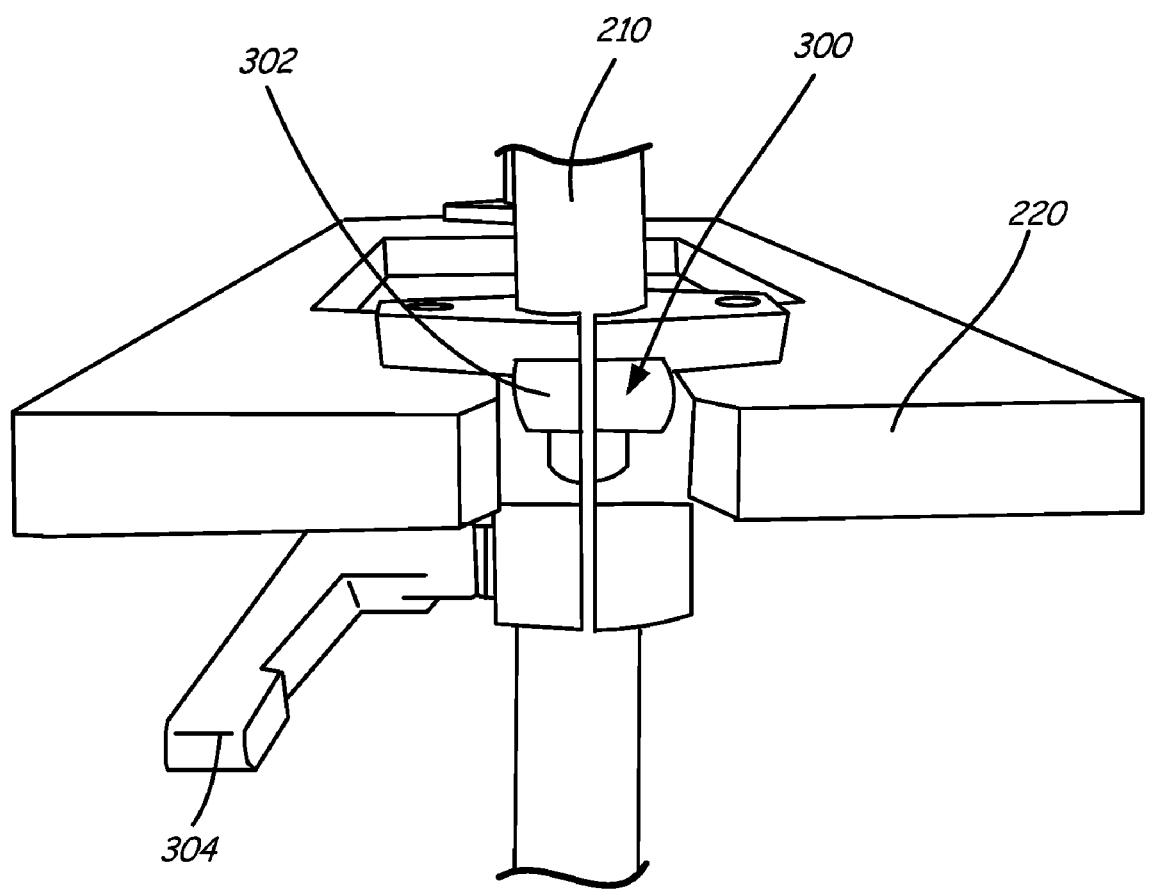
FIG. 15 illustrates a clamp mechanism for slidably connecting the elevated platform relative to guide rails of the test apparatus.

The height of platform 220 is adjustable along rails 210 via a clamp mechanism 300 shown in FIG. 15 to adjust the height of the acceleration path depending upon test specifications. As shown in FIG. 15, the clamp mechanism 300 includes a clamp 302 which, slidably couples the elevated platform 220 to guide rails 210 to slidably adjust the position of the platform 220 along the guide rails 210. At the desired position, the clamp 302 is tightened to lock the position of the platform 220. To adjust the position of the platform 220, the clamp 302 is released via lever 304 to slidably adjust the position or height of the platform 220 relative to platform 222 to set the acceleration path based upon the test specifications. Although a particular mechanism is shown to slidably connect the platform 220 relative to the guide rails 210, application is not limited to the specific embodiment shown.

It is to be understood that even though numerous characteristics and advantages of various embodiments of the invention have been set forth in the foregoing description, together with details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, the particular elements may vary depending on the particular application while maintaining substantially the same functionality without departing from the scope and spirit of the present invention. In addition, although the preferred embodiment described herein is directed to portable data storage device, it will be appreciated by those skilled in the art that the teachings of the present invention is not limited to the particular device shown.

What is claimed is:

1. A test apparatus comprising:
   an accelerator component movable along at least one rail to impart an acceleration to a test specimen along an acceleration path;
   a holder assembly coupled to the acceleration component and movable along the acceleration path therewith and the holder assembly including a holder that is selectively operable between a clamped mode and a differently configured unclamped mode to releasably hold the test specimen; and a release mechanism including a first release component coupled to the holder assembly and engageable with a second release component off-board from the accelerator component to operate the holder from the clamped mode to the unclamped mode and thereby release the test specimen from the holder assembly.

2. The test apparatus of claim 1 wherein the second release component is coupled to a platform elevated from a landing and the platform includes at least one end stop device configured to restrict movement of the holder assembly toward the landing.

3. The test apparatus of claim 1 and further comprising a platform elevated from a landing and the platform having an adjustable height.

4. The apparatus of claim 1 wherein the apparatus comprises:
    a sensor device; and
    a camera activated by the sensor device to capture one or more images of the test specimen proximate to a landing following release from the holder assembly.

5. The apparatus of claim 1 wherein the holder includes clamps coupled to clamp arms and the clamp arms are biased inwardly to hold the test specimen along the acceleration path in the clamped mode and the inward bias is released to release the test specimen from the holder assembly.

6. The test apparatus of claim 5 wherein the clamp arms of the holder assembly are biased inwardly via a spring biased locking mechanism.

7. The test apparatus of claim 6 wherein the release mechanism includes a camming assembly to release the spring biased locking mechanism.

8. The test apparatus of claim 7 wherein camming assembly includes a roller on a platform elevated from a landing which forms the second release component and an inclined camming surface coupled to the holder assembly which forms the first release component to release the spring biased locking mechanism.

9. The test apparatus of claim 8 wherein the inclined camming surface is formed on a flange configured to contact the roller to move one or more rods of the locking mechanism against the spring bias to release the test specimen.

10. The test apparatus of claim 3 and comprising a latch mechanism coupled to the platform and the latch mechanism is configured to releasably latch the accelerator component to the platform.

11. A test apparatus comprising:
    an accelerator assembly movable along an acceleration path to impart an acceleration to a test specimen coupled to a holder assembly including holder selectively operable between a holding mode and a differently configured release mode;
    a release mechanism switching the holder from the holding mode to the release mode to release the test specimen from the holder assembly to a landing while the test specimen is still in motion imparted by the accelerator assembly; and
    a roll device imparting a rotational shock to the test specimen following release of the test specimen from the holder assembly.

12. The apparatus of claim 11 wherein the roll device is coupled to the landing of the test apparatus.

13. The test apparatus of claim 11 wherein the accelerator assembly includes an accelerator component movable along the acceleration path under an influence of gravity and comprising at least one end stop device elevated from the landing and configured to restrict movement of the accelerator component beyond the at least one end stop device to the landing.

14. The test apparatus of claim 13 wherein the at least one end stop device is coupled to a platform elevated from the landing and the release mechanism includes a release component on the platform to release the test specimen from the holder assembly to the landing.

15. A method comprising:
    securing a test specimen having a shock absorber component to a holder assembly;
    accelerating the holder assembly along an acceleration path;
    releasing the test specimen from the holder assembly to a landing surface to test shock robustness of the test specimen; and
    determining shock robustness of the test specimen and using shock robustness data to design the shock absorber component of the test specimen.

16. The method of claim 15 wherein the test specimen includes a data storage device including at least one rotatable disc and the shock absorber component is enclosed in a casing to limit shock to the data storage device.

17. The method of claim 16 wherein the shock robustness is determined based upon whether an actuator mechanism of the data storage device unlatches and/or the shock absorber component "bottoms out".

18. The method of claim 15 and further comprising:
    introducing a rotational shock to the test specimen released from the holder assembly.

19. The method of claim 15 and further comprising:
    capturing one or more images of the test specimen following release from the holder assembly.

20. The method of claim 15 and comprising:
    detecting the test specimen following release from the holder assembly; and
    activating a camera to record one or more images of the test specimen.

* * * * *